(12) United States Patent
Yerebakan et al.

(10) Patent No.: US 11,176,188 B2
(45) Date of Patent: Nov. 16, 2021

(54) VISUALIZATION FRAMEWORK BASED ON DOCUMENT REPRESENTATION LEARNING

(71) Applicant: Siemens Healthcare GmbH, Erlangen (DE)

(72) Inventors: Halid Ziya Yerebakan, Indianapolis, IN (US); Yoshihisa Shinagawa, Downingtown, PA (US); Parmeet Singh Bhatia, Frazer, PA (US); Yiqiang Zhan, Berwyn, PA (US)

(73) Assignee: Siemens Healthcare GmbH, Erlangen (DE)

( * ) Notice: Subject to any disclaimer, the term of this patent is extended or adjusted under 35 U.S.C. 154(b) by 495 days.

(21) Appl. No.: 15/865,539

(22) Filed: Jan. 9, 2018

(65) Prior Publication Data
US 2018/0196873 A1 Jul. 12, 2018

Related U.S. Application Data

(60) Provisional application No. 62/445,062, filed on Jan. 11, 2017, provisional application No. 62/447,977, (Continued)

(51) Int. Cl.
*G06F 16/00* (2019.01)
*G06F 16/35* (2019.01)
(Continued)

(52) U.S. Cl.
CPC .......... *G06F 16/358* (2019.01); *G06F 16/35* (2019.01); *G06F 16/367* (2019.01); *G06F 16/93* (2019.01); *G06F 40/30* (2020.01); *G06K 9/00442* (2013.01); *G06K 9/00483* (2013.01); *G06K 9/627* (2013.01); *G06K 9/6215* (2013.01); *G06K 9/6226* (2013.01); *G06N 3/0445* (2013.01);
(Continued)

(58) Field of Classification Search
CPC ...... G06F 16/358; G06F 40/30; G06F 16/367; G16H 10/60; G16H 30/40; G16H 15/00; G06N 3/0454; G06N 7/005; G06N 3/08; G06N 3/0445
See application file for complete search history.

(56) References Cited

U.S. PATENT DOCUMENTS 8,132,104 B2 * 3/2012 Ash .................. G06F 40/174
715/728
9,659,560 B2 * 5/2017 Cao .................. G06F 40/40
(Continued)

OTHER PUBLICATIONS

Yerebakan, et al., "The Infinite Mixture of Infinite Gaussian Mixtures," Advances in Neural Information Processing Systems pp. 28-36, 2014.

*Primary Examiner* — Debbie M Le

(57) ABSTRACT

A visualization framework based on document representation learning is described herein. The framework may first convert a free text document into word vectors using learning word embeddings. Document representations may then be determined in a fixed-dimensional semantic representation space by passing the word vectors through a trained machine learning model, wherein more related documents lie closer than less related documents in the representation space. A clustering algorithm may be applied to the document representations for a given patient to generate clusters. The framework then generates a visualization based on these clusters.

20 Claims, 7 Drawing Sheets

Related U.S. Application Data filed on Jan. 19, 2017, provisional application No. 62/447,999, filed on Jan. 19, 2017.

(51) Int. Cl.

| | |
|---|---|
| *G16H 50/70* | (2018.01) |
| *G06K 9/00* | (2006.01) |
| *G06N 20/00* | (2019.01) |
| *G06F 16/93* | (2019.01) |
| *G06K 9/62* | (2006.01) |
| *G06F 16/36* | (2019.01) |
| *G16H 15/00* | (2018.01) |
| *G16H 30/40* | (2018.01) |
| *G06N 3/04* | (2006.01) |
| *G06N 3/08* | (2006.01) |
| *G06N 7/00* | (2006.01) |
| *G16H 10/60* | (2018.01) |
| *G06F 40/30* | (2020.01) |
| *G06N 20/10* | (2019.01) |
| *G06N 5/00* | (2006.01) |

(52) U.S. Cl.
CPC ............ *G06N 3/0454* (2013.01); *G06N 3/08* (2013.01); *G06N 7/005* (2013.01); *G06N 20/00* (2019.01); *G06N 20/10* (2019.01); *G16H 10/60* (2018.01); *G16H 15/00* (2018.01); *G16H 30/40* (2018.01); *G16H 50/70* (2018.01); *G06N 5/003* (2013.01)

(56) References Cited

U.S. PATENT DOCUMENTS

| | | | | |
|---|---|---|---|---|
| 10,354,182 | B2* | 7/2019 | Chang | G06F 16/951 |
| 10,606,946 | B2* | 3/2020 | Gao | G06F 40/268 |
| 2012/0008819 | A1* | 1/2012 | Ding | G06K 9/00335 |
| | | | | 382/100 |
| 2016/0335345 | A1* | 11/2016 | Wang | G06F 16/34 |
| 2017/0286835 | A1* | 10/2017 | Ho | G06F 16/367 |
| 2018/0121792 | A1* | 5/2018 | Tristan | G06N 3/0445 |
| 2018/0157944 | A1* | 6/2018 | Ashwin | H04W 12/08 |
| 2019/0188263 | A1* | 6/2019 | Ock | G06F 40/30 |

\* cited by examiner

VISUALIZATION FRAMEWORK BASED ON DOCUMENT REPRESENTATION LEARNING

CROSS-REFERENCE TO RELATED APPLICATIONS

This application claims the benefit of U.S. provisional application No. 62/447,977 filed Jan. 19, 2017, U.S. provisional application No. 62/447,999 filed Jan. 19, 2017 and U.S. provisional application No. 62/445,062 filed Jan. 11, 2017, the entire contents of which are incorporated herein by reference.

TECHNICAL FIELD

The present disclosure generally relates to digital data processing, and more particularly to a visualization framework that is based on document representation learning.

BACKGROUND

In radiology imaging, comparison studies for monitoring the progress of a disease of a patient provide indispensable information for medical treatment. Radiologists typically search for previous relevant reports (or documents) from a radiological database to perform such comparison. Despite providing hospital-specific templates for such reports, unstructured text format is still widely used due to its flexibility. Comparisons are time consuming processes, especially with senior patients who have crowded imaging histories. Thus, some critical information may be overlooked.

Automatic matching of reports is not trivial, since reports are generally kept in unstructured text format in radiology databases. Exact keyword matching is not directly useful since the same entities may be written in different names, such as "cardiac" and "heart". At the same time, many irrelevant reports may share the same keywords. Semantical understanding of the text is necessary to find the actual matching of reports that experts consider as similar.

SUMMARY

Described herein is a visualization framework based on document representation learning. The framework may first convert a free text document into word vectors using learning word embeddings. Document representations may then be determined in a fixed-dimensional semantic representation space by passing the word vectors through a trained machine learning model, wherein more related documents lie closer than less related documents in the representation space. A clustering algorithm may be applied to the document representations for a given patient to generate clusters. The framework then generates a visualization based on these clusters.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
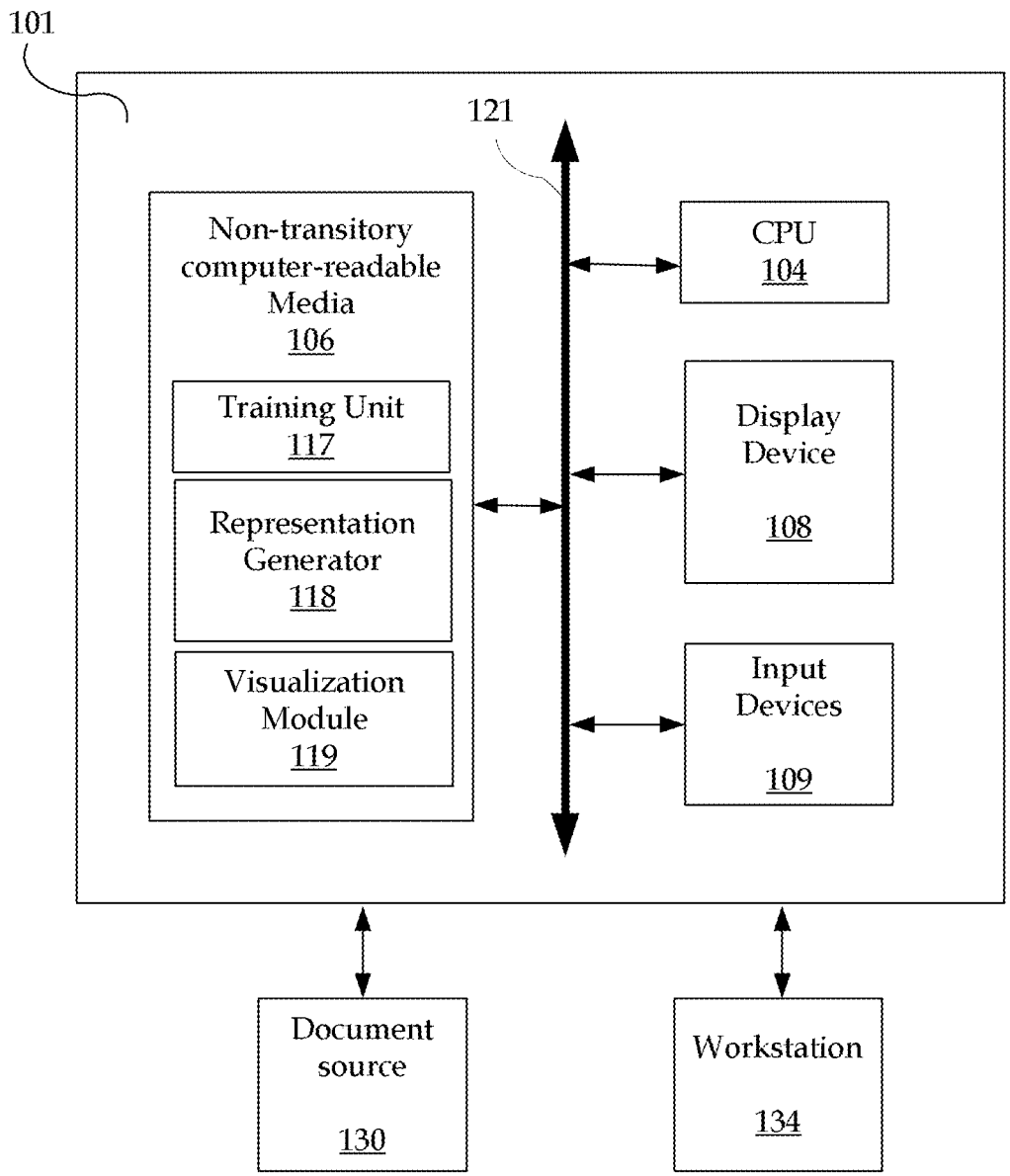
FIG. 1 shows a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-Dimensional image, the domain of the image is typically a 2- or 3-Dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displays as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

A document representation learning framework is presented herein. The framework learns a continuous, fixed-dimensional semantic representation (or projection) space for plain text documents (or reports). Clinically related documents lie close to each other with respect to a distance measure (e.g., Euclidian distance) in the representation space. In order to ensure that the similarity measure provided by the semantic representation is clinically meaningful, the framework may utilize weak label information encoded in previous comparisons provided by radiologists to supervise the representation learning.

Creating a semantic space for documents provides multiple potential benefits. First, it provides an abstraction from text, which may serve as an efficient semantic information retrieval tool. Similar documents may be automatically retrieved from such semantic space without incurring the overhead of manually selecting the studies of interest, thereby making the radiology workflow more efficient. In addition, semantic similarity measures allow patient level clustering of documents and analysis of patient population. Moreover, the abstraction may be used in a higher-level summarization of the patient through disease lines (or relevant report groups) or in a population study for medical research. These representations are not only useful to extract disease lines of a patient, but are also beneficial to understand the whole population for research purposes. The effectiveness of the framework has been evaluated by cross-validation experiments conducted based on a large number of radiology reports.

A visualization methodology is further presented herein to visualize different aspects of the radiology report corpus using the extracted document representations. One exemplary visualization uses time information and clustering to group the documents in the semantic representation space to show, for example, different disease lines (or clinically relevant document groups). This visualization is useful for concisely summarizing a patient's clinical history for diagnosis. Another exemplary visualization shows the hierarchical relationships of words according to their representations for a given corpus. This visualization is useful for concisely showing what kinds of diseases exist in the patient population in the corpus. Any nonparametric clustering algorithm that works on a continuous domain may be used to generate such visualization. These and other exemplary advantages and features will be described in more detail in the following description.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as document source 130 and workstation 134. In a networked deployment, computer system 101 may operate in the capacity of a server (e.g., thin-client server, such as Syngo® by Siemens Healthineers), a client user machine in server-client user network environment, or as a peer machine in a peer-to-peer (or distributed) network environment.

In one implementation, computer system 101 includes a processor device or central processing unit (CPU) 104 coupled to one or more non-transitory computer-readable media 106 (e.g., computer storage or memory device), display device 108 (e.g., monitor) and various input devices 109 (e.g., mouse, touchpad or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in one or more non-transitory computer-readable media 106. In particular, the present techniques may be implemented by a training unit 117, a representation generator 118 and a visualization module 119. Non-transitory computer-readable media 106 may include random access memory (RAM), read-only memory (ROM), magnetic floppy disk, flash memory, and other types of memories, or a combination thereof. The computer-readable program code is executed by CPU 104 to process data provided by, for example, document source 130. As such, the computer system 101 is a general-purpose computer system that becomes a specific-purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 106 may be used for storing image datasets, knowledge base, individual patient data, database of records or documents for patients (e.g., training data), and so forth. Such data may also be stored in an external document source 130. Document source 130 may be implemented using a database management system (DBMS) and residing on a memory, such as a hard disk, RAM, or removable media. Document source 130 may be implemented on one or more additional computer systems (e.g., cloud storage). For example, document source 130 may include a data warehouse system residing on a separate computer system, a picture archiving and communication system (PACS), or any other now known or later developed hospital, medical institution, medical office, testing facility, pharmacy or other medical patient record storage system.

The workstation 134 may include a computer and appropriate peripherals, such as a keyboard and display device, and can be operated in conjunction with the entire system 100. For example, the workstation 134 may communicate with document source 130 so that the documents or reports retrieved from document source 130 can be presented or displayed at the workstation 134. The workstation 134 may communicate directly with the computer system 101 to display processed data and/or output results. The workstation 134 may include a graphical user interface to receive user input via an input device (e.g., keyboard, mouse, touch screen voice or video recognition interface, etc.) to manipulate visualization and/or processing of the data.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
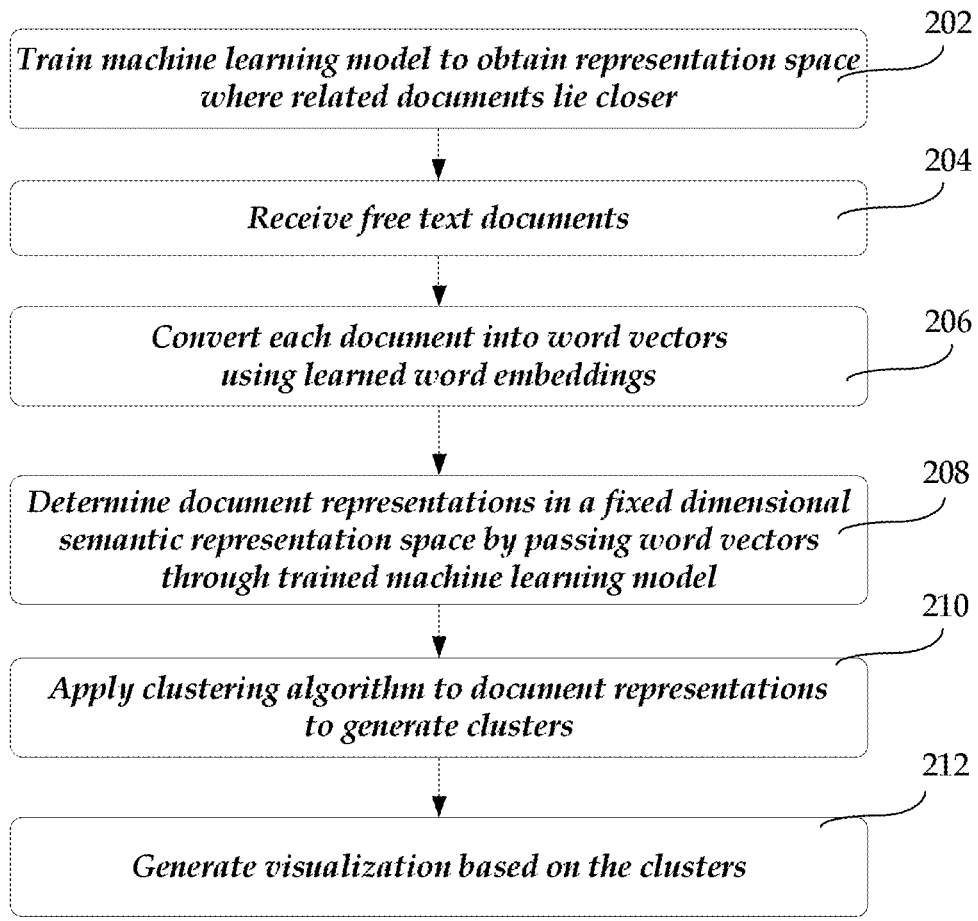
FIG. 2 shows an exemplary method performed by a computer system.

FIG. 2 shows an exemplary method 200 performed by a computer system. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, training unit 117 trains a machine learning model to obtain a representation space where related documents lie closer according to a distance measure (e.g., Euclidian distance). The machine learning model may be, for example, a recurrent neural network structure, such as a Siamese long short-term memory (LSTM). See Mueller, J., Thyagarajan, A., *Siamese recurrent architectures for learning sentence similarity*, In: AAAI, pp. 2786-2792 (2016), which is herein incorporated by reference for all purposes. Other types of machine learning models, such as convolutional neural networks (CNN) and recurrent neural networks (RNN), may also be used. A Siamese neural network is a class of neural network architectures that contain two or more identical (i.e., same configuration with same parameters and weights) subnetworks. Siamese structures can be easily used to estimate the semantic similarity of text data. They share the representation generation function that allows all documents to be represented in the same space. The similarity measure may be defined based on the distance in this representation space.

LSTM is a simple recurrent neural network which can be used as a building component or block (of hidden layers) for an eventually bigger recurrent neural network. A Siamese LSTM includes two parallel LSTM blocks with shared parameters. An LSTM block includes a memory cell that "remembers" a value for either long or short time periods, an input gate, an output gate and a forget gate that control or regulate information flow. The LSTM can be effectively used to learn very long-term dependencies with a sequence of words. The LSTM is capable of reducing variable length sequences to fixed-size (or fixed-dimensional) vectors. With these vectors, a Siamese LSTM can reduce a pair of reports to the same representation space.

Ground truth labels are used to train the Siamese LSTM. These labels may be used to create a document representation space in which more clinically relevant documents have a smaller distance. For a given pair of documents, a label is positive if one document is directly or indirectly referring to the other document in any direction. Positive labels may be created by extracting comparison study dates and matching these dates with document dates associated with the patient. Negative labels may be identified by applying a keyword match rule on a tagging system output. For example, a pair of reports that includes a thoracic CT study report of a lung and a plain X-ray radiograph of a tibia may be given a negative label. The labeling is not limited to this policy. It should be appreciated that other good quality clinical relevance labeling policies may also be applicable.

These positive and negative pairs of documents are used to learn parameters of the LSTM, such that positive pairs lie closer to each other and negative pairs are further from each other in the learned representation space. In some implementations, labels may be obtained from document referral information to generate clinically relevant document similarity measures for representation learning. These document referrals are useful for improving representations from a clinical perspective. However, it is also possible to generate document representations without them. To ensure compatibility of document representations in a comparison pair, both documents are passed as input to a Siamese LSTM network. Due to its recurrent structure, the LSTM network can handle input documents with variable sizes. This feature allows it to reduce variable-sized text input to fixed-dimensional continuous vectors. The LSTM network can learn long-term dependencies while being less prone to gradient problems in optimization.

During the training of the LSTM network, an objective function is optimized. In some implementations, a generalized logistic loss function is used as the objective function. Such objective function enforces a pair of documents with positive labels to have lower distance to each other than another pair of documents with negative labels. An exemplary objective function is shown as follows:

$$F(d,y)=(1/\beta)\log(1+e^{\beta(3/2)-y(\tau-d)}) \qquad (1)$$

where $\beta$ and $\tau$ are the hyper parameters, y is the label and d is the distance in the learned Euclidean representation space.

At 204, representation generator 118 receives one or more free text documents from document source 130. Free text documents contain unstructured data (e.g., text, graphics, images) that is not organized in a pre-defined manner. The free text documents may include radiology reports or other medical records. These documents may include studies on chest X-ray images, abdomen computed tomographic (CT) images, brain magnetic resonance (MR) images, and so forth.

The free text documents may be normalized by applying stemming and lowercase to the documents. Punctuations and numbers may be removed. The free text documents may be further preprocessed by using a natural language toolkit (NLTK). A natural language processing system may be used to extract information (e.g., pathology, anatomy, symptom, negation information) and tag the free text documents. Data to be fed to the trained machine learning model may be created using only tags or whole documents.

At 206, representation generator 118 converts each document into a sequence of word vectors using learned word embeddings. Word embeddings are used to map words or phrases in the documents to vectors of real numbers in a fixed-dimensional vector space. Even without training the machine learning model, a network with these learned word embeddings provides a reasonable similarity measure of the documents. It leads to more powerful results after training the whole network, as will be shown in the subsequent discussion herein.

In an exemplary implementation, the present network employs word embeddings with 100 dimensions. An exemplary group of models that can be used to produce word embeddings is word2vec. Word2vec models are shallow, two-layer neural networks that are trained to reconstruct linguistic contexts of words. The embedding vectors may be trained with a large biomedical corpus without additional supervision, and may be fixed during training of the representation learning algorithm. These embedding vectors provide a measure of semantical similarity between individual words or phrases.

Figure 3:
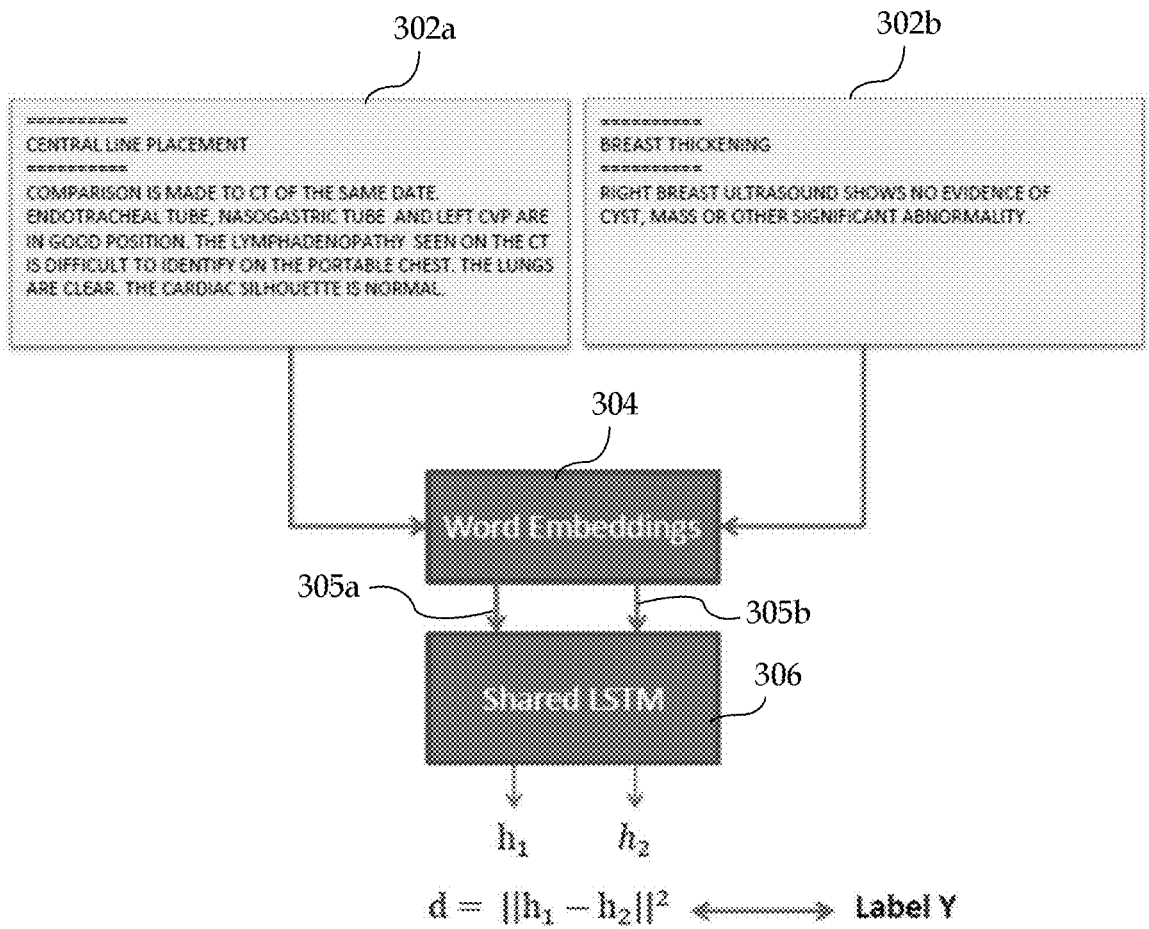
FIG. 3 shows an exemplary Siamese long short-term memory (LSTM) network.

At 208, representation generator 118 determines document representations (or vectors) in a continuous and fixed-dimensional semantic representation space by passing the word vectors through the trained machine learning model (e.g., Siamese LSTM network). FIG. 3 shows an exemplary Siamese LSTM network. A pair of documents 302$a$-$b$ are fed to pre-trained word embeddings 304 to generate word vectors 305$a$-$b$. The word vectors 305$a$-$b$ are provided as input to a trained Siamese LSTM network 306 that generates respective output vectors $h_1$ and $h_2$. The output vectors $h_1$ and $h_2$ are document representations that represent abstractions of the text, and they lie in the same high-dimensional representation space. The Euclidean distance d between the output vectors is provided by the following equation:

$$d=\|h_1-h_2\|^2 \quad (2)$$

The distance d is then used as the similarity value of the pair of documents.

Accordingly, the Siamese LSTM network 306 enforces closer embeddings for positive pairs while repelling negative pairs in the representation space. In other words, more related documents lie closer than less related documents in the representation space created by the Siamese LSTM network 306. Document representations may be advantageously obtained without engineering hand crafted features. Semantically relevant document representation may be useful in variety of clinical use cases, such as retrieval of clinically relevant reports and analysis of document distributions with respect to diseases and procedures.

Returning to FIG. 2, at 210, visualization module 119 applies a clustering algorithm to the document representations to generate clusters. The document representations are useful to obtain the different disease lines of a patient. The Euclidean distance in the representation space may be considered as a semantic similarity measure. Clustering in this representation space generates different document groups that tend to have likely comparisons.

In some implementations, a connected component-based clustering algorithm is applied to the document representations to generate clusters of documents for a given patient. The algorithm first calculates the distance matrix of the document representations, then applies a threshold to the distance matrix, followed by determination of connected components based on the binarized distance matrix. Each connected component represents one cluster. This method provides non-parametric clustering that allows different threshold levels to be applied via an interactive user interface presented at, for example, workstation 134, which can change the granularity in clustering quickly. It should be appreciated that other clustering algorithms may also be used.

In other implementations, visualization module 119 applies a multi-level clustering algorithm to the document representations to generate a hierarchy of clusters to explore, for example, hierarchical relations that most likely exist within radiology. Exploration of such hierarchical clusters within radiology data will further facilitate the understanding of correlations across different diseases and subtypes.

In the present data model, each cluster may include sub-clusters that are assumed to follow the Gaussian distribution in the new representation space. Gibbs sampling algorithm may be used for inference. A clustering algorithm that works on datasets with continuous space representations may be used to generate the hierarchy of clusters. An example of such a clustering algorithm is the Infinite Mixture of Infinite Gaussian Mixtures (I2GMM) algorithm, which is a Bayesian non-parametric method that can learn the number and shape of clusters from the data. See Yerebakan, H. Z., Rajwa, B., Dundar, M., *The infinite mixture of infinite gaussian mixtures*, Advances in Neural Information Processing Systems, pp. 28-36 (2014), which is herein incorporated by reference. I2GMM relies on Dirichlet Process (DP) Priors and Hierarchical Gaussian Data model. Prior distribution is the Chinese Restaurant Process (CRP) representation of the DP. I2GMM contains two layers for this prior. Dirichlet Process Priors model allows arbitrary numbers of clusters in training. I2GMM adds another layer to this process with Gaussian data model to achieve modeling non-Gaussian clusters.

Chinese restaurant process is prior over partitions. It is defined with parameter α that determines the probability of creating a new cluster. The probability distribution of clusters is given in following equations:

$$P(t=t_i)=n_i/(\alpha+n) \quad (3)$$

$$P(t=t_{new})=\alpha/(\alpha+n) \quad (4)$$

where t represents a cluster indicator variable, n represents the number of points, where $n_i$, represents the number of points in cluster i.

At 212, visualization module 119 generates a visualization based on the clusters. The visualization may be presented to the user at, for example, workstation 134. The visualization may be generated based on cluster information (e.g., document similarity) and temporal order information associated with the documents. In some implementations, the visualization facilitate navigation through documents by displaying documents in response to user selections of document representations in the visualization. The visualization may be generated in the form of, for example, a graph (e.g., 2D graph, scatter plot), table, chart, text, icons, and so forth. For example, the visualization may include a table where one axis (e.g., rows) represents the clusters and the other axis (e.g., columns) represents temporal order of the documents.

Figure 4A:
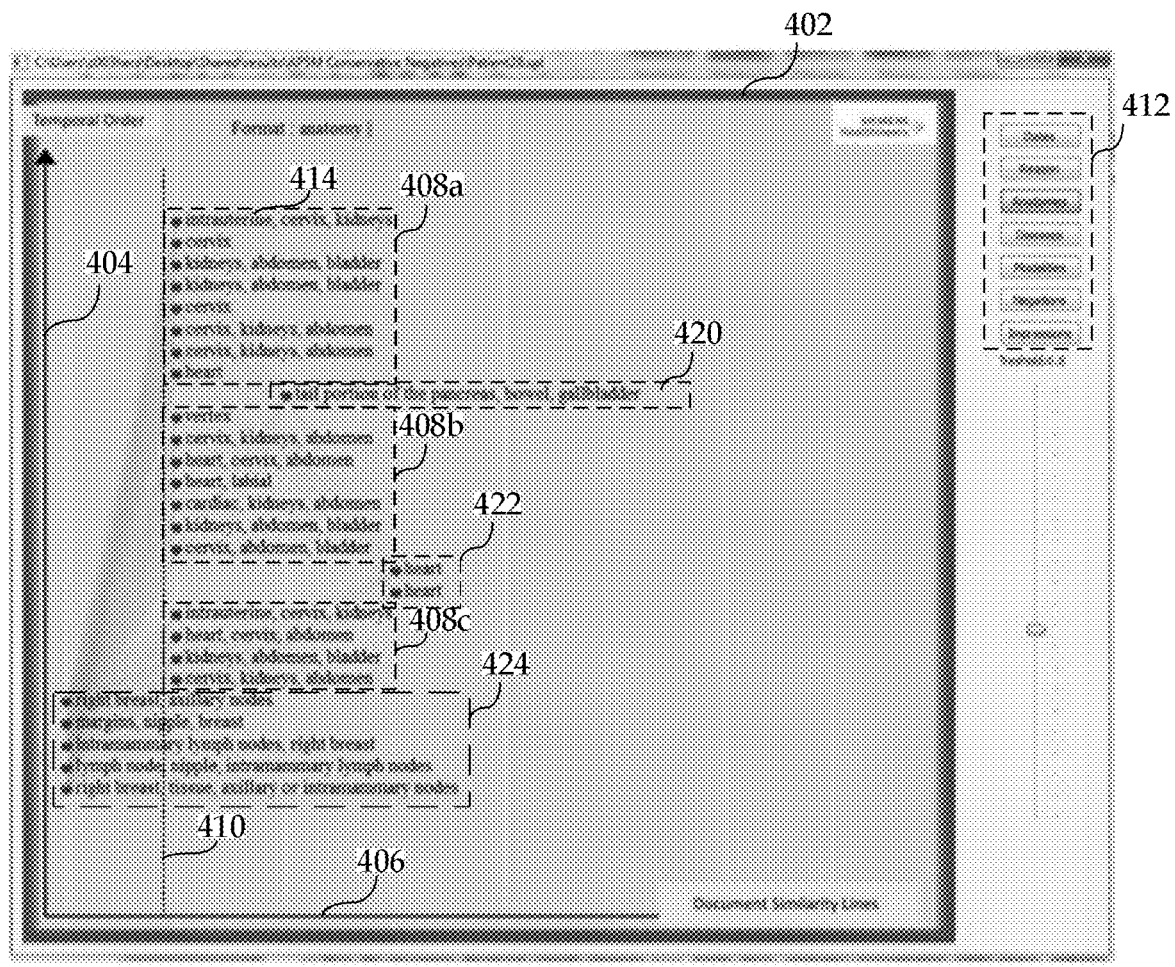
FIG. 4a shows an exemplary visualization of document clusters for a patient.

FIG. 4a shows an exemplary visualization 402 of document clusters for a patient. The visualization 402 is a two-dimensional graph, wherein one dimension (vertical axis y) 404 represents the temporal order, while another dimension (horizontal axis x) 406 represents document similarity lines. The clustering information is used to generate the visualization. All documents in a cluster are assigned unique y-coordinates and aligned along a similarity line according to the document dates. Therefore, the latest documents are placed near the top of the graph and the earliest documents are placed near the bottom of the graph. Each cluster represents a different x-coordinate. In this way, every cluster is represented by a distinct similarity line. Thus, the progression of each disease may be followed along the y-axis. For example, cluster 408a-c represents obstetric ultrasound studies and is aligned along similarity line 410. Other clusters 420, 422 and 424 are aligned along different similarity lines and represent abdominal check-up, heart catheterization and mammogram studies respectively.

Ground truth positive labels and negative labels may be represented by lines with different colors (e.g., blue, green), shadings or patterns for verification/validation purposes. Visualization module 119 may extract informative tags from the documents, such as dates, reasons, anatomies, diseases, modalities, negations and impressions, to represent the documents in the graph. The visualization may include a user interface with interactive buttons 412 that enable the user to select the type of tags to be displayed in the graph. As shown, the graph displays "anatomies" extracted from the documents in response to the user selection. As the pointer hovers over a text marker 414 representing a document, the entire document may be displayed in, for example, a tooltip. Visualization 402 is associated with a particular female patient with different disease lines. One of the lines (cluster 408a-c) is for a fetal regular check. She also had regular mammography studies (cluster 424). However, in one case she had problems which necessitated a CT image scan.

Figure 4B:
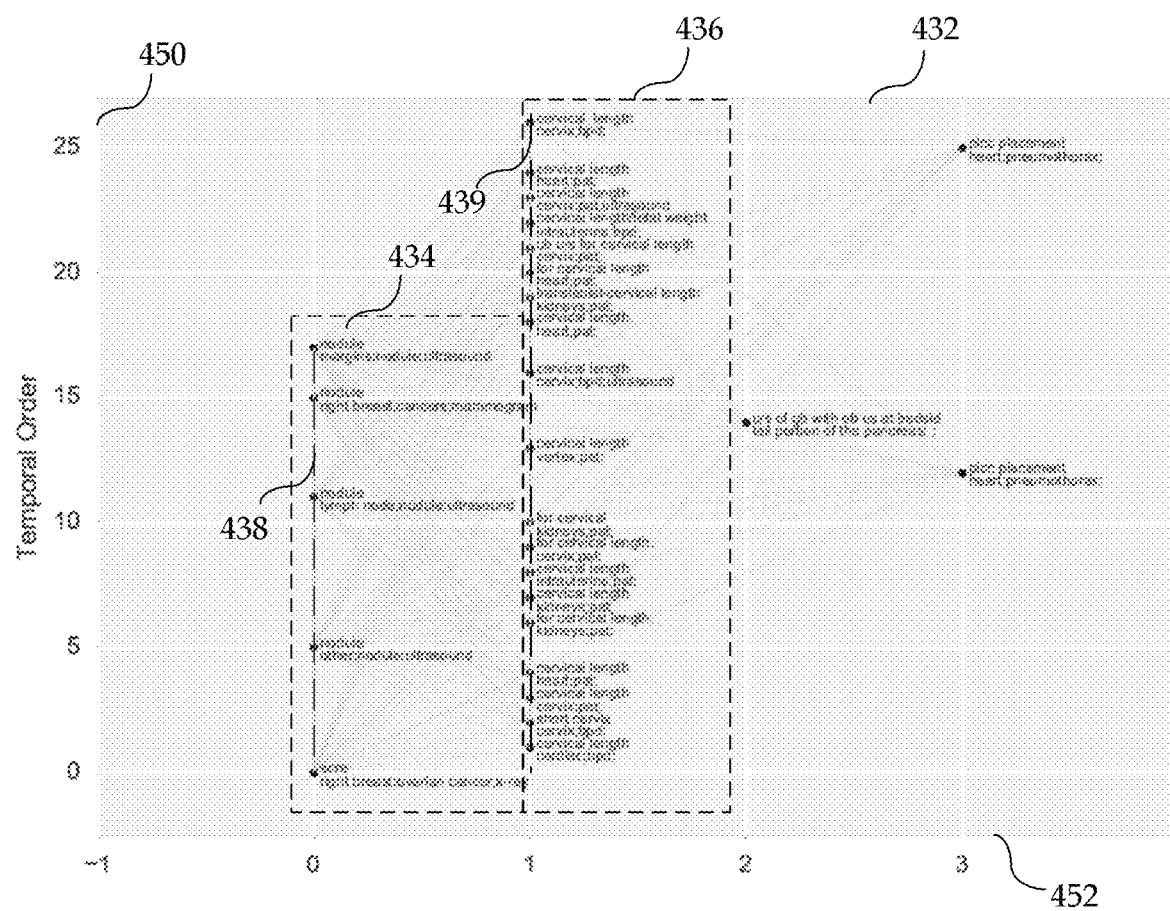
FIG. 4b shows another exemplary visualization of document clusters for a patient.

FIG. 4b shows another exemplary visualization 432 of document clusters for a patient. The visualization 432 is a two-dimensional graph, wherein the vertical axis y 450 represents the temporal order, while the horizontal axis 452 represents document similarity lines. Similar to visualization 402, each cluster (434, 436) is represented by a distinct similarity line (438, 439). Thus, the progression of each disease may be followed along the vertical axis. Comparison studies with ground truth labels match the clustering 434 and 436.

Visualization module 119 may generate another visualization to show the overall clustering of document representations associated with a population of patients. Relationships in a large corpus of cross-patient radiology reports advantageously facilitate understanding of disease patterns and their plausible treatments. Manual analysis of large radiology corpus is extremely time consuming or even impractical for most clinically relevant mining applications. The present framework simplifies comparison studies on radiology reports. This can reduce the resources required for analysis of patients, and facilitate understanding of the clinical status of patients.

Figure 5:
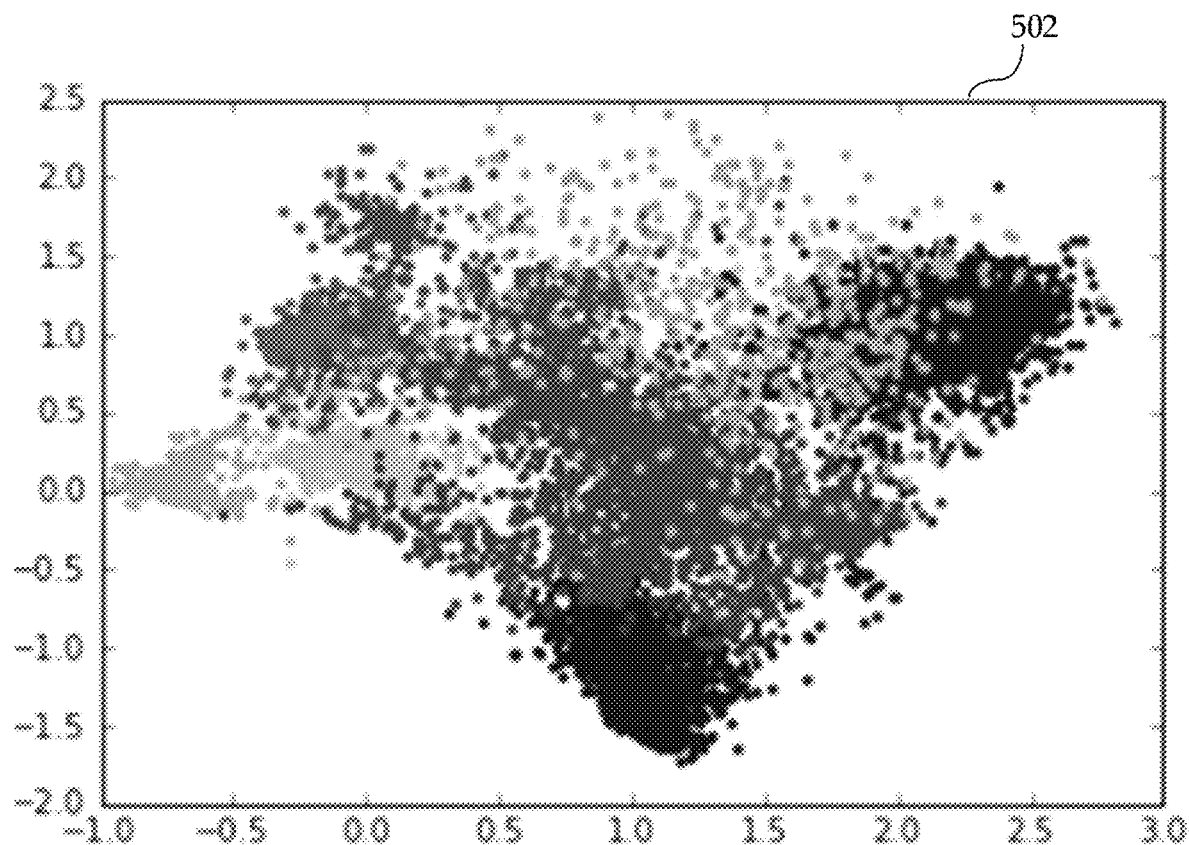
FIG. 5 shows an exemplary visualization of learned representations associated with a patient population.

FIG. 5 shows an exemplary visualization of learned document representations associated with a patient population. The hierarchical document representations $h_1$ or $h_2$ (see Equation 2) are projected into a two-dimensional space represented by a scatter plot. Each dot in the scatter plot represents a projected document representation. The scatter plot may use different colors or shadings for different clusters to show the overall grouping of medical document representations associated with a population of patients. The clustering algorithm allows for multi-modal and skewed clusters.

Figure 6:
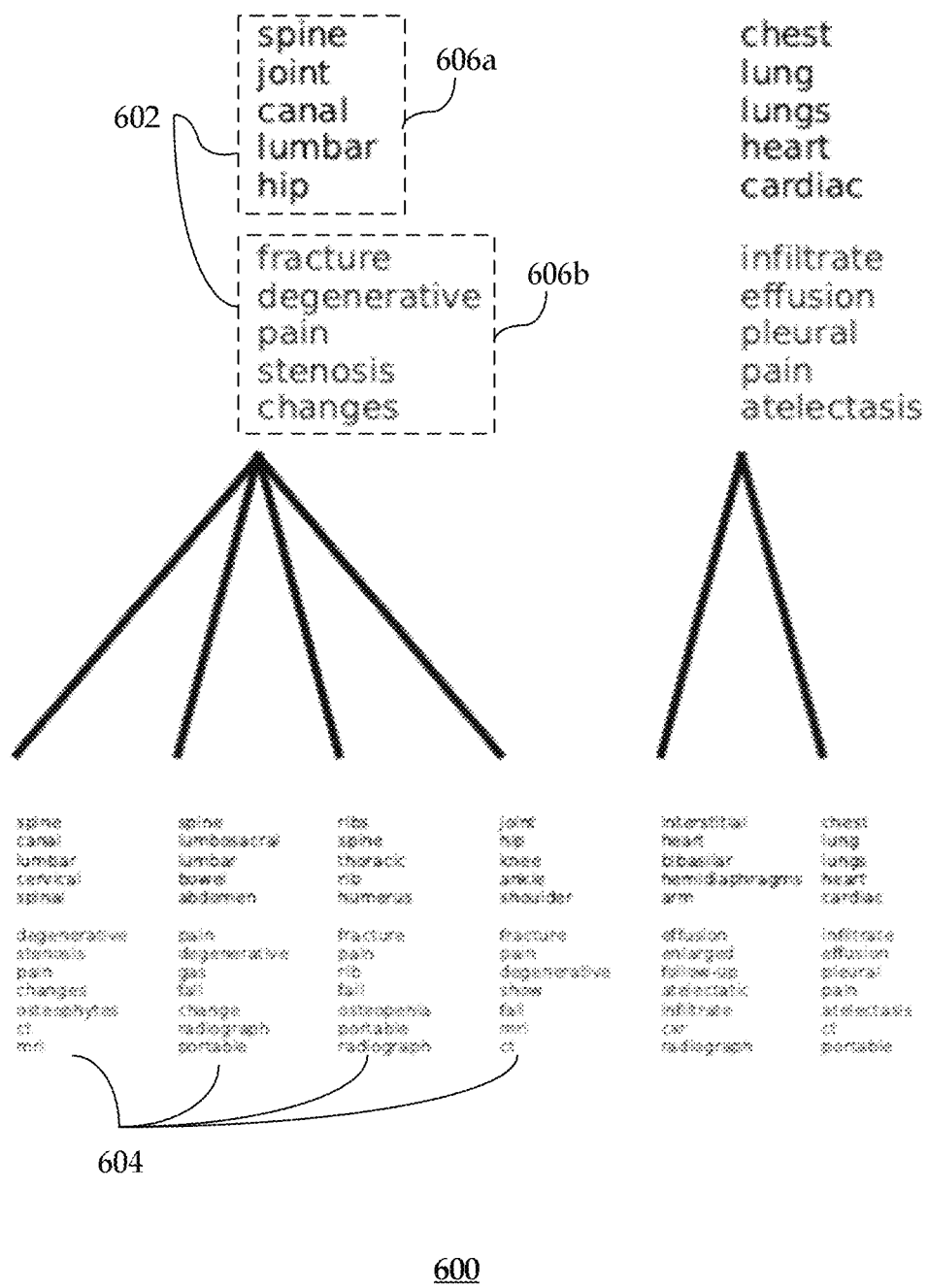
FIG. 6 shows an exemplary visualization of learned hierarchical representations.

FIG. 6 shows an exemplary visualization 600 of learned hierarchical representations. A portion of the tree structure based on a radiology corpus is shown. A parent node 602 of the tree structure represents a main cluster. The parent node 602 has multiple child nodes 604 that represent sub-clusters of documents. The parent node 602 and child nodes 604 are represented by one or more types of keywords extracted from associated documents. Keywords 606a are determined based on the most frequent anatomies, while keywords 606b are determined by the most frequently tagged disease words in the corresponding cluster or sub-cluster of documents.

To test the performance of the representation learning framework, a corpus containing a large number of anonymized radiology reports was obtained from hospitals. Single admissions were not used in the representation learning. Positive labels were created by extracting comparison studies in each patient history. Indirect links were added in these referrals to extend positive labels. Treating all remaining pairs as negative created a bias towards the negative class, since the number of pairs grew quadratically with the number of reports. Instead, clear negatives were provided by applying a rule-based method on the remaining pairs based on extracted tag information of words. For this reason, supervision was considered weak. However, as results show, this information was sufficient to determine the semantic similarity between documents. Vocabulary size was limited to a hundred thousand words in embeddings with lowercase normalization.

The hyper parameters were chosen as follows: $\tau=0.25$, separation=1, $\beta=2$. The network was trained for 10 epochs with a batch size of 200. Accuracy was used as a metric for evaluation of semantic representations of the documents. The classification was based on Euclidean distance in learned space. Documents lower than a distance of 0.5 were considered as positive pairs. Data was split randomly into training and testing sets at patient level. Under this classification rule, the Siamese LSTM representation learning algorithm achieved an accuracy of 0.976 over the validation set.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:
1. A visualization system, comprising:
   a non-transitory memory device for storing computer readable program code; and
   a processor device in communication with the memory device, the processor being operative with the computer readable program code to perform steps including
      receiving a free text document,
      converting the free text document into word vectors using learned word embeddings, wherein the learned word embeddings provide a measure of semantical similarity between individual words or phrases, determining, by a trained neural network, document representations in a fixed-dimensional semantic representation space by passing the word vectors through the trained neural network, wherein more related documents lie closer than less related documents in the representation space, applying a multi-level clustering algorithm to the document representations to generate a hierarchy of clusters, wherein at least one of the clusters is a group of document representations that tend to have likely comparisons, and generating a visualization based on the hierarchy of clusters.

2. The system of claim 1 wherein the processor is operative with the computer readable program code to apply the multi-level clustering algorithm by applying an Infinite Mixture of Infinite Gaussian Mixtures (I2GMM) algorithm to the document representations.

3. The system of claim 1 wherein the processor is operative with the computer readable program code to generate the visualization based on the hierarchy of clusters by generating a scatter plot or tree structure of the hierarchy of clusters.

4. A computer-implemented method, comprising:
receiving a free text document;
converting the free text document into word vectors using learned word embeddings, wherein the learned word embeddings provide a measure of semantical similarity between individual words or phrases;
determining, by a trained machine learning model, document representations in a fixed-dimensional semantic representation space by passing the word vectors through the trained machine learning model, wherein more related documents lie closer than less related documents in the representation space;
applying a clustering algorithm to the document representations to generate clusters, wherein at least one of the clusters is a group of document representations that tend to have likely comparisons; and
generating a visualization based on the clusters.

5. The method of claim 4 further comprises training the machine learning model to obtain the representation space.

6. The method of claim 5 wherein training the machine learning model comprises training a neural network.

7. The method of claim 5 wherein training the machine learning model comprises training a Siamese long short-term memory (LSTM) network.

8. The method of claim 5 wherein training the machine learning model comprises:
passing pairs of documents with positive and negative labels as input to the machine learning model; and
optimizing an objective function that enforces a pair of documents with positive labels to have lower distance to each other than another pair of documents with negative labels.

9. The method of claim 5 wherein training the machine learning model comprises obtaining labels from document referral information to generate clinically relevant document similarity measures for representation learning.

10. The method of claim 4 wherein converting the free text document into the word vectors comprises passing the free text document through a trained word2vec model.

11. The method of claim 4 wherein applying the clustering algorithm to the document representations to generate the clusters comprises applying a connected component-based clustering algorithm to the document representations.

12. The method of claim 11 wherein applying the connected component-based clustering algorithm comprises:
calculating a distance matrix of the document representations;
applying a threshold to the distance matrix; and
determining connected components based on the distance matrix.

13. The method of claim 4, wherein applying the clustering algorithm to the document representations to generate the clusters comprises applying a multi-level clustering algorithm to the document representations to generate a hierarchy of clusters.

14. The method of claim 13 where applying the multi-level clustering algorithm comprises applying an Infinite Mixture of Infinite Gaussian Mixtures (I2GMM) algorithm to the document representations.

15. The method of claim 4 wherein generating the visualization based on the clusters comprises generating a graph based on temporal order and cluster information.

16. The method of claim 4 wherein generating the visualization based on the clusters comprises generating a user interface that enables a user to select a type of document tags to be displayed in the visualization to represent documents.

17. The method of claim 4 wherein generating the visualization based on the clusters comprises projecting the document representations into a two-dimensional space represented by a scatter plot associated with a population of patients.

18. The method of claim 4 wherein generating the visualization based on the clusters comprises generating a tree structure representing documents associated with a population of patients.

19. The method of claim 18 wherein nodes of the tree structure are represented by one or more keywords extracted from associated documents.

20. One or more non-transitory computer readable media embodying a program of instructions executable by machine to perform steps comprising:
receiving a free text document;
converting the free text document into word vectors using learned word embeddings, wherein the learned word embeddings provide a measure of semantical similarity between individual words or phrases;
determining, by a trained machine learning model, document representations in a fixed-dimensional semantic representation space by passing the word vectors through the trained machine learning model, wherein more related documents lie closer than less related documents in the representation space;
applying a clustering algorithm to the document representations to generate clusters, wherein at least one of the clusters is a group of document representations that tend to have likely comparisons; and
generating a visualization based on the clusters.

* * * * *